(12) United States Patent
Egwuagu et al.

(10) Patent No.: US 9,629,897 B2
(45) Date of Patent: Apr. 25, 2017

(54) METHODS OF PRODUCING AND USING REGULATORY B-CELLS

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Charles Emeka Egwuagu, Silver Spring, MD (US); Ren-Xi Wang, Beijing (CN); Cheng-rong Yu, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/396,475

(22) PCT Filed: Apr. 11, 2013

(86) PCT No.: PCT/US2013/036175
§ 371 (c)(1),
(2) Date: Oct. 23, 2014

(87) PCT Pub. No.: WO2013/162905
PCT Pub. Date: Oct. 31, 2013

(65) Prior Publication Data
US 2015/0110737 A1 Apr. 23, 2015

Related U.S. Application Data

(60) Provisional application No. 61/637,915, filed on Apr. 25, 2012.

(51) Int. Cl.
*C12N 5/0781* (2010.01)
*A61K 38/20* (2006.01)
*A61K 35/17* (2015.01)
*C07K 14/54* (2006.01)
*A61K 38/16* (2006.01)
*C12N 7/00* (2006.01)

(52) U.S. Cl.
CPC .............. *A61K 38/20* (2013.01); *A61K 35/17* (2013.01); *A61K 38/162* (2013.01); *A61K 38/208* (2013.01); *C07K 14/54* (2013.01); *C07K 14/5428* (2013.01); *C12N 5/0635* (2013.01); *C12N 7/00* (2013.01); *C12N 2501/2312* (2013.01); *C12N 2501/2327* (2013.01); *C12N 2501/2335* (2013.01); *C12N 2501/50* (2013.01); *C12N 2501/65* (2013.01); *C12N 2510/00* (2013.01); *C12N 2710/16232* (2013.01)

(58) Field of Classification Search
CPC ...... A61K 38/20; A61K 35/17; A61K 38/208; C07K 14/54; C07K 14/5428; C12N 2501/2335; C12N 5/0635
See application file for complete search history.

(56) References Cited

U.S. PATENT DOCUMENTS

| | | | |
|---|---|---|---|
| 8,080,555 B2 | 12/2011 | Zacharie et al. | |
| 2007/0299026 A1* | 12/2007 | Liew | C07K 14/52 514/44 R |
| 2011/0135666 A1* | 6/2011 | Tedder | A61K 35/17 424/173.1 |
| 2011/0206759 A1* | 8/2011 | Swartz | A61K 39/001 424/450 |
| 2014/0011755 A1* | 1/2014 | Stein | A61K 31/585 514/26 |

FOREIGN PATENT DOCUMENTS

JP 2008500812 A 1/2008

OTHER PUBLICATIONS

Allman et al., "Alternative routes to maturity: branch points and pathways for generating follicular and marginal zone B cells," *Immunol. Rev.*, 197, 147-160 (2004).
Amadi-Obi et al., "TH17 cells contribute to uveitis and scleritis and are expanded by IL-2 and inhibited by IL-27/STAT1," *Nat. Med.*, 13 (6), 711-718 (2007).
Carter et al., "Mice lacking endogenous IL-10-producing regulatory B cells develop exacerbated disease and present with an increased frequency of Th1/Th17 but a decrease in regulatory T cells," *J. Immunol.*, 186 (10), 5569-5579 (2011), with supplmentary material.
Caspi et al., "A new model of autoimmune disease. Experimental autoimmune uveoretinitis induced in mice with two different retinal antigens," *J. Immunol.*, 140 (5), 1490-1495 (1988).
Chan et al., "Pathology of experimental autoimmune uveoretinitis in mice," *J. Autoimmun.*, 3 (3), 247-255 (1990).
Chaturvedi et al., "Cutting edge: Human regulatory T cells require IL-35 to mediate suppression and infectious tolerance," *J. Immunol.*, 186 (12), 6661-6666 (2011), with supplementary material.
Collison et al., "Interleukin-35: odd one out or part of the family?," *Immunol. Rev.*, 226, 248-262 (2008).
Collison et al., "The inhibitory cytokine IL-35 contributes to regulatory T-cell function," *Nature*, 450 (7169), 566-569 (2007).
Commins et al., "The extended IL-10 superfamily: IL-10, IL-19, IL-20, IL-22, IL-24, IL-26, IL-28, and IL-29," *J. Allergy Clin. Immunol.*, 121 (5), 1108-1111 (2008).

(Continued)

*Primary Examiner* — Daniel C Gamett
(74) *Attorney, Agent, or Firm* — Leydig, Voit & Mayer, Ltd.

(57) ABSTRACT

The invention is directed to a method of preparing B-cells that produce interleukin-10 (IL-10), or IL-10 per se, which comprises contacting one or more B-cells ex vivo with an isolated interleukin-35 (IL-35) protein, and culturing the one or more B-cells under conditions to provide one or more B-cells that produce IL-10. The invention also is directed to a method of suppressing the proliferation of lymphocytes in vitro or in vivo by contacting lymphocytes with an isolated IL-35 protein. The invention further is directed to a method of suppressing autoimmunity in a mammal by administering to the mammal an IL-35 protein or IL-10-producing B-cells.

24 Claims, 10 Drawing Sheets

(56) References Cited

OTHER PUBLICATIONS

Devergne et al., "Epstein-Barr virus-induced gene 3 and the p35 subunit of interleukin 12 form a novel heterodimeric hematopoietin," *Proc Nat. Aca. Sci.*, 94 (22),12041-12046 (1997).

Ding et al., "Regulatory B cells are identified by expression of TIM-1 and can be induced through TIM-1 ligation to promote tolerance in mice," *J. Clin. Invest.*, 121 (9), 3645-3656 (2011).

Fillatreau et al., "B cells regulate autoimmunity by provision of IL-10," *Nat. Immunol.*, 3 (10), 944-950 (2002).

Fillatreau et al., "Not always the bad guys: B cells as regulators of autoimmune pathology," *Nat. Rev. Immunol.*, 8 (5), 391-397 (2008).

Gee et al., "The IL-12 family of cytokines in infection, inflammation and autoimmune disorders," *Inflamm. Allergy Drug Targets*, 8 (1), 40-52 (2009).

Genbank NCBI Accession No. AAH08209.1, printed Jul. 15, 2006.
Genbank NCBI Accession No. ABK41923.1, printed Nov. 13, 2006.
Genbank NCBI Accession No. NM_000882.3, printed May 11, 2014.
Genbank NCBI Accession No. NM_005755.2, printed Apr. 27, 2014.
Genbank NCBI Accession No. NP_001152896.1, printed Feb. 15, 2015.
Genbank NCBI Accession No. NP_032377.1, printed Feb. 15, 2015.

Hunter, "New IL-12-family members: IL-23 and IL-27, cytokines with divergent functions," *Nature Rev. Immunol.*, 5 (7), 521-531 (2005).

International Preliminary Report on Patentability in International Patent Application No. PCT/US2013/036175, issued Oct. 28, 2014.

International Search Report in International Patent Application No. PCT/US2013/036175, mailed Jul. 2, 2013.

Kumar et al., "Long-term culture of primary B cells and in vitro expression of an exogenous gene," *Immunol. Lett.*, 47 (3), 193-197 (1995).

Lu et al., "Quantification of parapapillary atrophy and optic disc," *Invest. Ophthalmol. Vis. Sci.*, 52 (7), 4671-4677 (2011).

Luger et al., "Either a Th17 or a Th1 effector response can drive autoimmunity: conditions of disease induction affect dominant effector category," *J. Exp. Med.*, 205 (4), 799-810 (2008).

Mauri et al., "The 'short' history of regulatory B cells," *Trends Immunol.*, 29 (1), 34-40 (2008).

Mizoguchi et al., "A case for regulatory B cells," *J. Immunol.*, 176 (2), 705-710 (2006).

Mosser et al., "Interleukin-10: new perspectives on an old cytokine," *Immunol. Rev.*, 226, 205-218 (2008).

Myung et al., "Evaluation of vascular disease progression in retinopathy of prematurity using static and dynamic retinal images," *Am. J. Ophthalmol.*, 153 (3), 544-551 (2011).

Niedbala et al., "IL-35 is a novel cytokine with therapeutic effects against collagen-induced arthritis through the expansion of regulatory T cells and suppression of Th17 cells," *Eur. J. Immuno.*, 37 (11), 3021-3029 (2007).

Nussenblatt, "Proctor Lecture. Experimental autoimmune uveitis: mechanisms of disease and clinical therapeutic indications," *Invest. Ophthalmol. Vis. Sci.*, 32 (13), 3131-3141 (1991).

Nussenblatt, "The natural history of uveitis," *Int. Ophthalmol.*, 14 (5-6), 303-308 (1990).

Olkhanud et al., "Tumor-evoked regulatory B cells promote breast cancer metastasis by converting resting $CD4^+$ T cells to T-regulatory cells," *Cancer Res.*, 71 (10), 3505-3515 (2011).

Paques et al., "Panretinal, high-resolution color photography of the mouse fundus," *Invest. Ophthalmol. Vis. Sci.*, 48 (6), 2769-2774 (2007).

Riley et al., "Human T regulatory cell therapy: take a billion or so and call me in the morning," *Immunity*, 30 (5), 656-665 (2009).

Sabat et al., "Biology of interleukin-10," *Cytokine Growth Factor Rev.*, 21 (5), 331-344 (2010).

Schioppa et al., "B regulatory cells and the tumor-promoting actions of TNF-α during squamous carcinogenesis," *Proc. Natl. Acad. Sci. USA*, 108 (26), 10662-10667 (2011).

Stefanova et al., "Self-recognition promotes the foreign antigen sensitivity of naive T lymphocytes," *Nature*, 420 (6914), 429-434 (2002).

Tadmor et al., "The absence of B lymphocytes reduces the number and function of T-regulatory cells and enhances the anti-tumor response in a murine tumor model," *Cancer Immunol. Immunother.*, 60 (5), 609-619 (2011).

Vasconcellos et al., "IL-12p35 Subunit contributes to autoimmunity by limiting IL-27-Driven Regulatory Response," *J. Immunol.*, 187 (6), 3402-3412 (2011).

Whitlock et al., "Long-term culture of B lymphocytes and their precursors from murine bone marrow," *Proc. Natl. Acad. Sci. USA*, 79 (11), 3608-3612 (1982).

Whitlock et al., "Murine B cell lymphopoiesis in long term culture," *J. Immunol. Methods*, 67 (2), 353-369 (1984).

Wolf et al., "Experimental autoimmune encephalomyelitis induction in genetically B cell-deficient mice," *J. Exp. Med.*, 184 (6), 2271-2278 (1996).

Written Opinion of the International Searching Authority in International Patent Application No. PCT/US2013/036175, dated Oct. 25, 2014.

Xu et al., "A clinical grading system for retinal inflammation in the chronic model of experimental autoimmune uveoretinitis using digital fundus images," *Exp. Eye Res.*, 87 (4), 319-326 (2008).

Fujita H et al, "Mechanisms of allergen-specific immunotherapy", *Clinical and Translational Allergy* 2(1):2 (2012).

Kochetkova I et al, "IL-35 Stimulation of CD39+ Regulatory T Cells Confers Protection against Collagen II-Induced Arthritis via the Production of IL-10", *The Journal of Immunology* 184(12):7144-7153 (2010).

Australian Intellectual Property Office, Examination Report dated Nov. 24, 2016, 4 pages.

Office Action, Japanese Patent Application No. 2015-509008, dated Jan. 17, 2017, 14 pages.

Mizogushi et al. "Chronic Intestinal Inflammatory Condition Generates IL-10-Producing Regulatory B Cell Subset Characterized by CD1d Upregulation" *Immunity* 16:219-230 (Feb. 2002).

"Discovery of the mechanism that produces suppresive cytokine IL-10 that calms down immune response—clock gene transcription factor E4BP4 regulates suppression of Immune response—" *Riken* (Apr. 4, 2011) http://www.riken.jp/pr/press/2011/20110404/>retrieved Jan. 11, 2017.

* cited by examiner

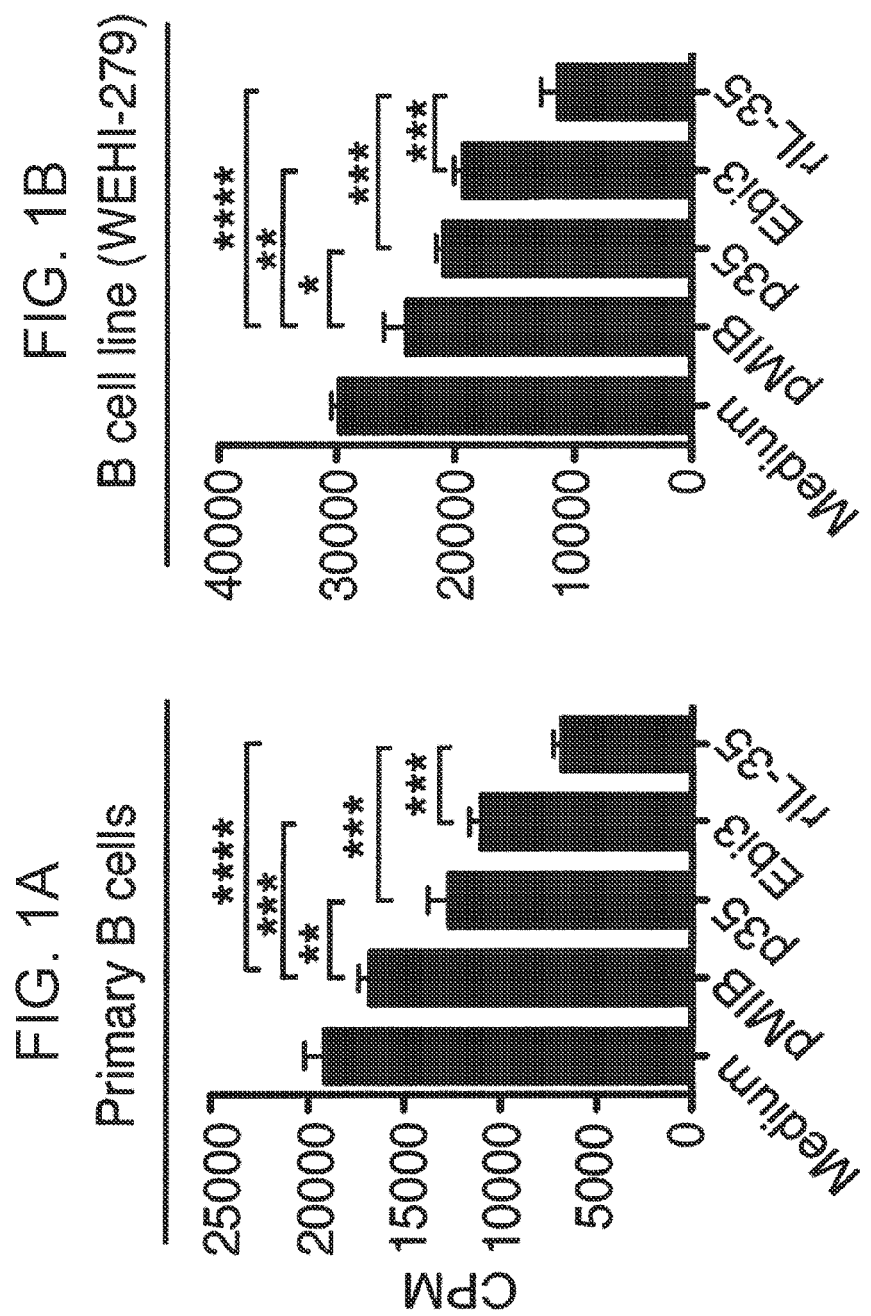

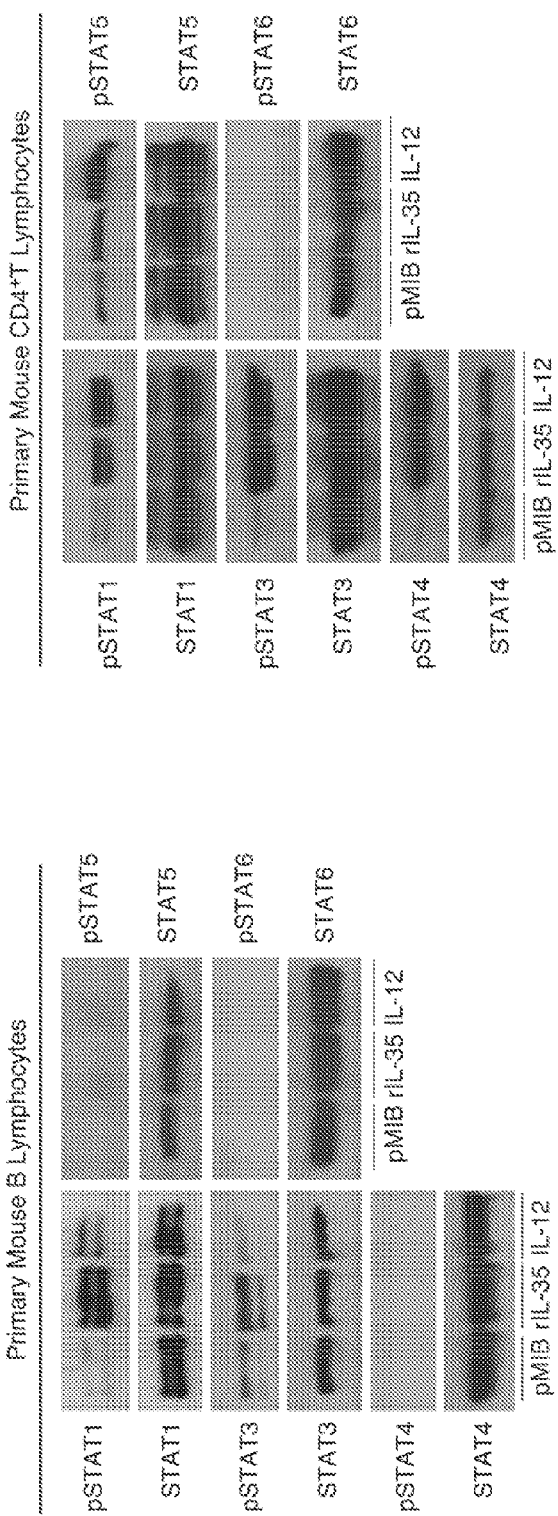

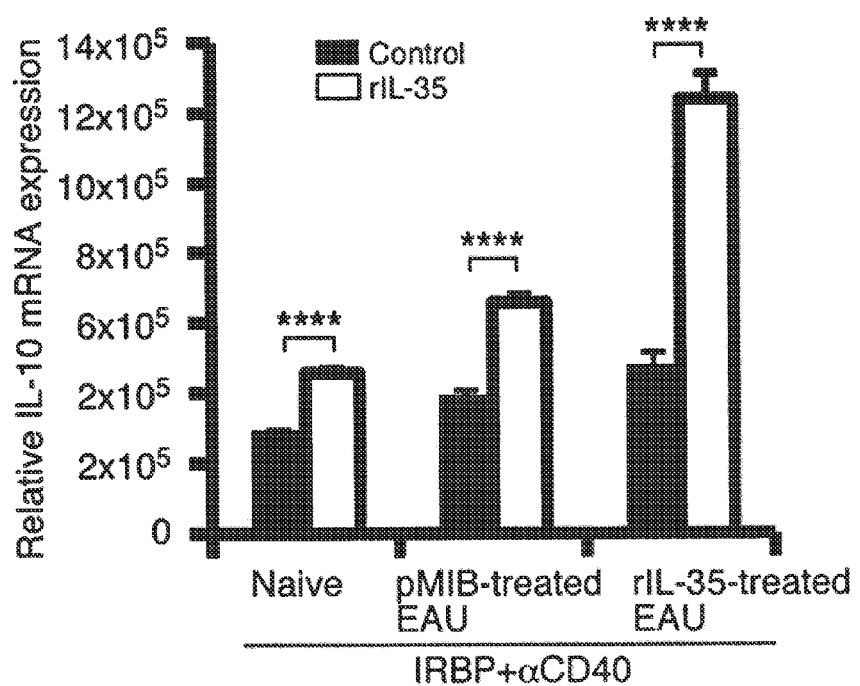

SEQUENCE LISTING

<160> NUMBER OF SEQ ID NOS: 2

<210> SEQ ID NO 1
<211> LENGTH: 648
<212> TYPE: DNA
<213> ORGANISM: Homo sapiens

<400> SEQUENCE: 1

```
atgtgtcaat cacgctacct cctcttttg gccacccttg ccctcctaaa ccacctcagt      60
ttggccaggg tcattccagt ctctggacct gccaggtgtc ttagccagtc ccgaaacctg     120
ctgaagacca cagatgacat ggtgaagacg gccagagaaa aactgaaaca ttattcctgc     180
actgctgaag acatcgatca tgaagacatc acacgggacc aaaccagcac attgaagacc     240
tgtttaccac tggaactaca caagaacgag agttgcctgg ctactagaga gacttcttcc     300
acaacaagag ggagctgcct gcccccacag aagacgtctt tgatgatgac cctgtgcctt     360
ggtagcatct atgaggactt gaagatgtac cagacagagt tccaggccat caacgcagca     420
cttcagaatc acaaccatca gcagatcatt ctagacaagg gcatgctggt ggccatcgat     480
gagctgatgc agtctctgaa tcataatggc gagactctgc gccagaaacc tcctgtggga     540
gaagcagacc cttacagagt gaaaatgaag ctctgcatcc tgcttcacgc cttcagcacc     600
cgcgtcgtga ccatcaacag ggtgatgggc tatctgagct ccgcctga                  648
```

<210> SEQ ID NO 2
<211> LENGTH: 687
<212> TYPE: DNA
<213> ORGANISM: Homo sapiens

<400> SEQUENCE: 2

```
atgtccaagc tgctcttcct gtcacttgcc ctctgggcca gccgctcccc tggttacact      60
gaaacagctc tcgtggctct aagccagccc agagtgcaat gccatgcttc tcggtatccc     120
gtggccgtgg actgctcctg gactcctctc caggctccca actccaccag atccacgtcc     180
ttcattgcca cttacaggct cggtgtggcc acccagcagc agagccagcc ctgcctacaa     240
cggagccccc aggcctcccg atgcaccatc cccgacgtgc acctgttctc cacggtgccc     300
tacatgctaa atgtcactgc agtgcaccca ggcggcgcca gcagcagcct cctagccttt     360
gtggctgagc gaatcatcaa gccggaccct ccggaaggcg tgcgcctgcg cacagcggga     420
cagcgcctgc aggtgctctg gcatcccct gcttcctggc ccttcccgga catcttctct     480
ctcaagtacc gactccgcta ccggcgccga ggagcctctc acttccgcca ggtgggaccc     540
attgaagcca cgactttcac cctcaggaac tcgaaacccc atgccaagta ttgcatccag     600
gtgtcagctc aggacctcac agattatggg aaaccaagtg actggagcct ccctgggcaa     660
gtagaaagtg caccccataa gccctga                                         687
```

METHODS OF PRODUCING AND USING REGULATORY B-CELLS

CROSS-REFERENCE TO RELATED APPLICATIONS

This patent application is a U.S. National Phase of International Patent Application No. PCT/US2013/036175, filed Apr. 11, 2013, which claims the benefit of U.S. Provisional Patent Application No. 61/637,915 filed Apr. 25, 2012, each of which is incorporated by reference herein in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,315 Byte ASCII (Text) file named "718623_ST25.TXT," created on Oct. 23, 2014.

BACKGROUND OF THE INVENTION

A distinct population of B-cells which suppress the progression of and/or enhance the recovery from acquired immune-mediated inflammations has recently been identified and named regulatory B-cells, or "Bregs." Regulatory B-cells have been shown to play a key role in controlling autoimmunity, and their absence or loss is implicated in the etiology of several autoimmune diseases (see, e.g., Fillatreau et al., *Nat. Rev. Immunol.*, 8: 391-397 (2008), Carter et al., *J. Immunol.*, 186: 5569-5579 (2011), and Ding et al., *J. Clin. Invest.*, 121: 3645-3656 (2011)). Regulatory B-cells appear to control autoimmunity by various mechanisms, including the production of interleukin-10 (IL-10), secondary antigen presentation, and interaction with other immune cells either directly or through secreted antibodies (see, e.g., Mizoguchi et al., *J. Immunol.*, 176: 705-710 (2006)).

Aberrant elevation of regulatory B-cell levels can prevent sterilizing immunity to pathogens, and tumor-induced regulator B-cells have recently been implicated in carcinogenesis (see, e.g., Tadmor et al., *Caner Immunol. Immunother.*, 60: 609-619 (2011), Schioppa et al., *Proc. Natl. Acad. Sci. USA*, 108: 10662-10667 (2011), and Mauri et al., *Trends Immunol.*, 29: 34-401 (2008)). In particular, regulatory B-cells have been shown to promote breast cancer metastasis by converting resting $CD4^+$ T-cells to T-regulatory cells (Tregs) (see, e.g., Olkhanud et al., *Cancer Res.*, 71: 3505-3515 (2011)).

Regulatory B-cells are a rare B-cell population, and the physiological signals underlying their production are not completely understood. The identification of these signals may allow for the development of therapeutics based on regulatory B-cells to treat a variety of diseases.

Thus, there remains a need for methods of producing and using regulatory B-cells. This invention provides such methods.

BRIEF SUMMARY OF THE INVENTION

The invention provides a method of preparing B-cells that produce interleukin-10 (IL-10), which comprises contacting one or more B-cells ex vivo with an isolated interleukin-35 (IL-35) protein, and culturing the one or more B-cells under conditions to provide one or more B-cells that produce IL-10.

The invention provides a method of producing IL-10, which comprises contacting one or more B-cells ex vivo with an isolated interleukin-35 (IL-35) protein, and culturing the one or more B-cells under conditions to provide one or more B-cells that produce IL-10.

The invention provides a method of suppressing the proliferation of lymphocytes in vitro or in vivo, which comprises contacting one or more lymphocytes with an isolated IL-35 protein, whereby the proliferation of lymphocytes is suppressed.

The invention provides a method of suppressing autoimmunity in a mammal, which comprises administering to a mammal an isolated IL-35 protein, whereupon B-cells producing IL-10 are produced in the mammal and autoimmunity is suppressed in the mammal.

The invention provides a method of suppressing autoimmunity in a mammal, which comprises administering to a mammal B-cells which produce IL-10, whereby autoimmunity is suppressed in the mammal.

The invention also provides an isolated IL-35 protein for the suppression of autoimmunity in a mammal, and isolated B-cells which produce IL-10 for the suppression of autoimmunity in a mammal.

BRIEF DESCRIPTION OF THE SEVERAL VIEWS OF THE DRAWINGS

FIGS. 1A and 1B are graphs which depict experimental data illustrating the proliferation of sorted CD19+ primary B-cells and WEHI-279 B-cells, respectively, in response to pMIB, p35, Ebi3 or rIL-35.

FIG. 2D is an image of a Western blot which depicts experimental data illustrating that rIL-35 induced STAT activation of primary B-cells. FIG. 2E is an image of a Western blot which depicts experimental data illustrating that rIL-35 induced STAT activation of primary T-cells.

FIG. 3D is a graph which depicts experimental data illustrating the expression of IL-10 in mice treated with rIL-35 during EAU induction.

DETAILED DESCRIPTION OF THE INVENTION

Figure 1D:
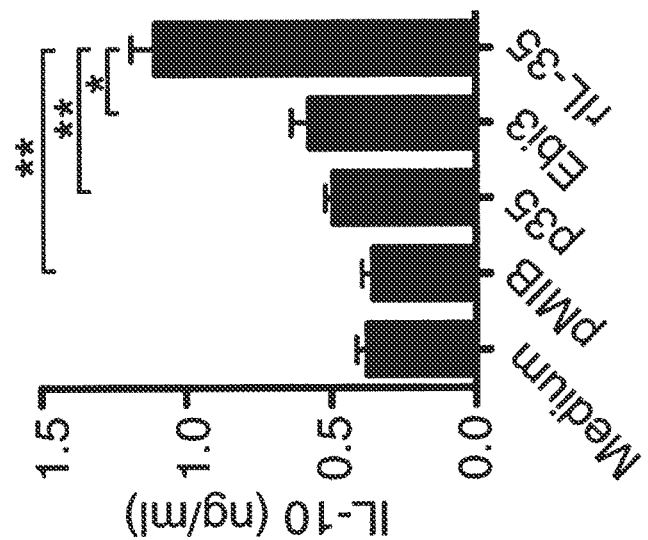
FIG. 1D is a graph which depicts experimental data illustrating the production of IL-10 by primary B-cells in response to pMIB, p35, Ebi3, or rIL-35 as assayed by ELISA.

The invention provides a method of preparing B-cells that produce interleukin-10 (IL-10), as well as a method of producing IL-10. In addition, the invention provides a method of suppressing the proliferation of lymphocytes in vitro or in vivo and a method of suppressing autoimmunity in a mammal.

The inventive method of preparing B-cells that product IL-10 comprises contacting one or more B-cells ex vivo with an isolated interleukin-35 (IL-35) protein, and culturing the one or more B-cells under conditions to provide one or more B-cells that produce IL-10. Similarly, the inventive method of producing IL-10 comprises contacting one or more B-cells ex vivo with an isolated interleukin-35 (IL-35) protein, and culturing the one or more B-cells under conditions to provide one or more B-cells that produce IL-10.

B-cells (or B-lymphocytes) are lymphocytes which differentiate into plasma cells that secrete antibodies. Immature B-cells are produced in the bone marrow of most mammals. After reaching the IgM$^+$ immature stage in the bone marrow, these immature B-cells migrate to the spleen, where they are called transitional B-cells, and some of these cells eventually differentiate into mature B lymphocytes (see, e.g., Allman et al., *Immunol. Rev.,* 197: 147-160 (2004)). B-cell development occurs through several stages, with each stage representing a change in the genome content of antibody genes.

Mature B-cells can be classified as either plasma B-cells (also known as plasma cells, plasmocytes, or effector B-cells) or memory B-cells. Plasma B-cells are large B-cells that have been exposed to antigen and produce and secrete large amounts of antibodies. Plasma B-cells are short-lived and undergo apoptosis when the antigen that induced a particular immune response is eliminated. In contrast, memory B-cells are long-lived stimulated B-cells that are primed for rapid response to a repeated exposure of a priming antigen. Memory B-cells are generated in lymphoid tissue after B-cell activation/proliferation and reside in the bone marrow, lymph nodes, and spleen (see, e.g., Janeway et al. (eds.), *Immunobiology,* 5$^{th}$ ed., Garland Publishing, New York, N.Y. (2001)).

Each B-cell has a unique receptor protein on its surface that will bind to one particular antigen, which is referred to as the B-cell receptor (BCR). The BCR is a membrane-bound immunoglobulin, which allows the distinction of B-cells from other types of lymphocytes, and is the main protein involved in B-cell activation. Once a B-cell encounters its cognate antigen and receives an additional signal from a T helper cell, the B-cell can further differentiate into either a plasma B-cell or a memory B-cell. The B-cell may differentiate into a plasma or memory B-cell directly, or the B-cell may undergo intermediate differentiation steps, called germinal center reactions, in which a B-cell undergoes somatic hypermutation of the variable region of an immunoglobulin gene, and possibly class switching. Other functions of B-cells include antigen presentation, cytokine production, and lymphoid tissue organization.

A small subset of immunoregulatory B-cells that play a role in immune regulations resulting in the complete recovery from acute experimental autoimmune encephalomyelitis (EAE) were first described by Wolf et al., *J. Exp. Med.,* 184: 2271-2278 (1996). Data from other experimental models of chronic inflammation indicate that B-cells can be divided into functionally distinct regulatory subsets that are capable of inhibiting inflammatory responses and inducing immune tolerance. These "regulatory" B-cells (or "Bregs") have subsequently been found to express interleukin-10 (IL-10) (see, e.g., Fillatreau et al., *Nat. Immunol.,* 3: 944-950 (2002)). Thus, in the context of the invention, a "regulatory B-cell" is a B-cell that produces and secretes IL-10.

The inventive method comprises contacting one or more B-cells ex vivo with an isolated interleukin-35 (IL-35) protein, and culturing the one or more B-cells under conditions to provide one or more B-cells that produce IL-10. Interleukin-35 (IL-35) is a member of the IL-12 family of heterodimeric cytokines and is composed of Ebi3, a β chain subunit encoded by the Epstein-Barr virus (EBV)-induced gene 3 (also known as IL27b), and the IL12p35 α subunit encoded by IL-12α (see, e.g., Collison et al., *Nature,* 450: 566-569 (2007); Hunter et al., *Nature Reviews,* 5: 521-531 (2005); Devergne et al., *Proc. Natl. Acad. Sci. USA,* 94: 12041-12046 (1997); and Niedbala et al., Eur. J. Immunol., 37, 3021-3029 (2007)). IL-35 is produced by regulatory T-cells (Treg) and is required for the immunosuppressive activities of Tregs (see, e.g., Collison et al., supra, and Chaturvedi et al., *J. Immunol.,* 186: 6661-6666 (2011)).

The isolated IL-35 protein can be a native IL-35 that is isolated from regulatory T-cells which naturally produce IL-35. In this embodiment, the IL-35 protein preferably is isolated from a mammal (e.g., a human or a mouse). Alternatively, the isolated IL-35 can be a recombinant IL-35 protein (rIL-35) generated using routine molecular biology techniques. A recombinant IL-35 protein can contain all or a portion of a native IL-35 protein isolated from a human or a mouse. For example, a recombinant IL-35 protein can contain an entire native human IL-35 protein or an entire native mouse IL-35 protein. In another embodiment, a recombinant IL-35 protein can contain a portion of a native IL-35 protein isolated from a human and a portion of a native IL-35 protein isolated from a mouse (i.e., a "chimeric" IL-35 protein). One of ordinary skill in the art will appreciate that a recombinant IL-35 protein can contain other elements that optimize the expression and/or stability of the IL-35 protein in B-cells. In a preferred embodiment, the isolated IL-35 protein is a recombinant fusion protein comprising an IL-12p35 α subunit protein and an Epstein-Barr virus (EBV)-induced gene 3 (Ebi3) protein. Nucleic acid sequences that encode an IL-12p35 α subunit include, for example SEQ ID NO: 1, and NCBI Accession No. NM_000882.3. Nucleic acid sequences that encode an Ebi3 protein include, for example, SEQ ID NO: 2, and NCBI Accession No. NM_005755.2. Amino acid sequences of the IL-12p35 α subunit and the Ebi3 protein also are known and publicly available (see, e.g., NCBI Accession Nos. NP_001152896.1 and NP_032377.1 (IL-12p35 α) and NCBI Accession Nos. ABK41923.1 and AAH08209.1 (Ebi3)).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more)

amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The one or more B-cells are contacted ex vivo. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context.

The isolated IL-35 protein can be introduced into a cell, preferably a B-cell, using any suitable method known in the art. For example, a nucleic acid sequence encoding an IL-35 protein can be introduced into the cells by "transfection," "transformation," or "transduction." The terms "transfection," "transformation," or "transduction," as used herein, refer to the introduction of one or more exogenous polynucleotides into a host cell by physical or chemical methods. Many transfection techniques are known in the art and include, for example, calcium phosphate DNA co-precipitation (see, e.g., *Methods in Molecular Biology*, Vol. 7, E. J. Murray (ed.), *Gene Transfer and Expression Protocols*, Humana Press (1991)), DEAE-dextran, electroporation, cationic liposome-mediated transfection, tungsten particle-facilitated microparticle bombardment (see, e.g., Johnston, *Nature*, 346: 776-777 (1990)), and strontium phosphate DNA co-precipitation (see, e.g., Brash et al., *Mol. Cell Biol.*, 7: 2031-2034 (1987)). Alternatively, the one or more B-cells can be cultured in a medium that contains suitable amounts of the isolated IL-35 protein. For example, the B-cell can be provided in a culture medium, and the IL-35 protein can be introduced into the culture medium per se or as a solution of the IL-35 protein in an appropriate solvent. The selection of suitable methods for transformation, culture, amplification, screening, and purification of B-cells are known in the art (see, e.g., Kumar et al., *Immunol. Lett.*, 47(3): 193-197 (1995); Whitlock et al., *Proc. Natl. Acad. Sci. USA*, 79(11): 3608-3612 (1982); Whitlock et al., *J. Immunol. Methods*, 67(2): 353-369 (1984); and Janeway et al., supra).

The one or more B-cells preferably are obtained or derived from a mammal, more preferably a mouse, and most preferably a human. The one or more B-cells can be primary B-cells. The term "primary cell" refers to a cell that is isolated directly from living tissue (e.g., from a biopsy) and established for growth in vitro or ex vivo. In the context of the invention, primary B-cells can be isolated from any suitable source, including, for example, umbilical cord blood, peripheral blood, and spleen, and are available from a variety of commercial sources. Alternatively, the one or more B-cells are derived from a B-cell line or a cell line of pre-B lymphocyte origin. Such cell lines are available from the American Type Culture Collection (ATCC, Manassas, Va.) and include, for example, RAMOS cells (ATCC CRL-1596), Daudi cells (ATCC CCL-213), Jiyoye cells (ATCC CCL-87), MPC-11 cells (ATCC CCL-167), EB-3 cells (ATCC CCL-85), RPMI 8226 cells (ATCC CCL-155), Raji cells (CCL-86), and derivatives thereof.

The one or more B-cells are cultured under conditions so that one or more of the B-cells produce interleukin-10 (IL-10). IL-10 is a Type II cytokine and the founding member of a family of cytokines that include IL-19, IL-20, IL-22, IL-24, IL-26, IL-28, and IL-29 (Commins et al., *J. Allergy Clin. Immunol.*, 121: 1108-1111 (2008)). All of these cytokines bind to receptors with similar structures and activate the Janus kinase (JAK)/signal transducer and activator of transcription (STAT) signaling pathways. IL-10 exhibits the most potent anti-immune and anti-inflammatory activity of all the family members. The main biological function of IL-10 appears to be exerted on dendritic cells (DCs) and macrophages. IL-10 is a potent inhibitor of antigen presentation as well as the production of proinflammatory cytokines (see, e.g., Mosser and Zhang, *Immunol. Rev.*, 226: 205-218 (2008)). IL-10 is produced by several types of immune and non-immune cells, such as, for example, T-helper type 2 (Th2) cells, subsets of regulatory T-cells, $CD8^+$ T-cells, human B-cells, monocytes, some subsets of dendritic cells, granulocytes, keratinocytes, epithelial cells, and tumor cells (Mosser and Zhang, supra).

The inventive method of suppressing the proliferation of lymphocytes in vitro or in vivo comprises contacting one or more lymphocytes with an isolated IL-35 protein, whereby the proliferation of lymphocytes is suppressed.

The term "proliferation," as used herein, encompasses any aspect of the growth and reproduction of lymphocytes, including, for example, cell division (i.e., mitosis), cell growth (e.g. increase in cell size), and an increase in genetic material (e.g., prior to cell division). Proliferation of lymphocytes is "suppressed" if lymphocyte proliferation is reduced by at least about 10% (e.g., at least about 15%, at least about 30%, or at least about 20%), at least about 50% (e.g., at least about 60%, at least about 70%, or at least about 80%), or at least about 90% (e.g., at least about 95% or 100%) in response to IL-35 as compared to lymphocyte proliferation in the absence of IL-35. Preferably, lymphocyte proliferation is reduced by at least about 25% (e.g., at least about 35%, at least about 40%, or at least about 45%) in response to IL-35 as compared to lymphocyte proliferation in the absence of IL-35. More preferably, lymphocyte proliferation is reduced by at least about 50% (e.g., at last about 55%, at least about 65%, or at least about 75%) in response to IL-35 as compared to lymphocyte proliferation in the absence of IL-35. Most preferably, lymphocyte proliferation is reduced by at least about 80% (e.g., at least about 85%, at least about 95%, or about 100%) in response to IL-35 as compared to lymphocyte proliferation in the absence of IL-35. Lymphocyte proliferation can be measured using a variety of cell proliferation assays known in the art, many of which are available from commercial sources. Such assays include, for example, BrdU cell proliferation assays, $^3$H-thymidine incorporation assays, and tetrazolium salt (MTT) cell proliferation assays.

Lymphocytes are white blood cells that include natural killer (NK) cells, T-cells (also referred to as T-lymphocytes), and B-cells (also referred to a B-lymphocytes). NK cells are a part of the innate immune system and play a major role in defending a host from both tumors and virally infected cells. T-cells and B-cells are the major cellular components of the adaptive immune response and are involved in cell-mediated immunity and humoral immunity, respectively. In a preferred embodiment, the lymphocytes that are contacted with IL-35 are B-cells, T-cells, or B-cells and T-cells. The inventive method comprises contacting one or more lymphocytes with an isolated IL-35 protein in vivo or in vitro. When the method is carried out in vitro, any suitable method known in the art, such as those discussed herein, can be used to contact the lymphocytes with an isolated IL-35 protein (e.g., cell culture in the presence of IL-35).

Preferably, the one or more lymphocytes are contacted with IL-35 in vivo, desirably inside a mammal, preferably a mouse, and most preferably a human. In this manner, the isolated IL-35 protein is delivered to the mammal in the form of a composition. Preferably, the composition is a pharmaceutically acceptable (e.g., physiologically acceptable) composition, which comprises a carrier, preferably a pharmaceutically (e.g., physiologically acceptable) carrier, and the isolated IL-35 protein. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

The inventive method of suppressing autoimmunity in a mammal comprises administering to a mammal an isolated IL-35 protein, whereupon B-cells producing IL-10 are produced in the mammal and autoimmunity is suppressed in the mammal. Alternatively, or in addition, the inventive method of suppressing autoimmunity in a mammal comprises administering to a mammal B-cells which produce IL-10, whereby autoimmunity is suppressed in the mammal. The invention also provides an isolated IL-35 protein for the suppression of autoimmunity in a mammal, as well as isolated B-cells which produce IL-10 for the suppression of autoimmunity in a mammal. Descriptions of the isolated IL-35 protein and IL-10-producing B-cells, and components thereof, set forth above in connection with other embodiments of the invention also are applicable to those same aspects of the aforesaid method.

The term "autoimmunity," as used herein, refers to the failure of an organism (e.g., a human) to recognize its own constituent parts as self, which results in an immune response against the organism's own cells and tissues. In other words, autoimmunity is an adaptive immune response directed against "self" antigens and is marked by the production of "autoantibodies." Low levels of autoimmunity have been shown to aid in the recognition of neoplastic cells by CD8$^+$ T-cells, thereby reducing the incidence of cancer. In addition, low levels of autoimmunity may play a role in allowing a rapid immune response in the early stages of an infection when the availability of foreign antigens limits the response (i.e., when few pathogens are present) (see, e.g., Stefanova et al., *Nature*, 420 (6914): 429-434 (2002)). Therefore, low levels of autoimmunity may be beneficial. High levels of autoimmunity, however, typically are pathogenic and lead to autoimmune disease.

"Autoimmune disease" refers to any one of a group of diseases or disorders in which tissue injury is associated with a humoral and/or cell-mediated immune response to body constituents or, in a broader sense, an immune response to self. The pathological immune response may be systemic or organ specific. For example, the immune response directed against self may affect joints, skin, the myelin sheath that protects neurons, the kidneys, the liver, the pancreas, the thyroid, the adrenals, and ovaries. Immune complex formation plays a role in the etiology and progression of autoimmune disease. Increased immune complex formation correlates with the presence of antibodies directed to self (autoantibodies). The presence of autoantibodies can contribute to tissue inflammation either as part of an immune complex or unbound to antigen (free antibody). In some autoimmune diseases, the presence of free autoantibody contributes significantly to disease pathology. Another aspect of the etiology and progression of autoimmune disease is the role of proinflammatory cytokines. Under normal circumstances, proinflammatory cytokines such as tumor necrosis factor-α (TNF-α) and interleukin-1 (IL-1) play a protective role in the response to infection and cellular stress. However, the pathological consequences which result from chronic and/or excessive production of TNF-α and IL-1 are believed to underlie the progression of many autoimmune diseases such as rheumatoid arthritis, Crohn's disease, inflammatory bowel disease, and psoriasis. Other proinflammatory cytokines involved in autoimmune disease include interleukin-6, interleukin-8, interleukin-17, and granulocyte-macrophage colony stimulating factor (see, e.g., U.S. Pat. No. 8,080,555).

The inventive methods, isolated IL-35 protein, and isolated B-cells which produce IL-10 can be used to suppress autoimmunity associated with any autoimmune disease. There are more than 80 known autoimmune diseases known in the art, examples of which include multiple sclerosis (MS), insulin-dependent diabetes mellitus, systemic lupus erythematosus (SLE), psoriasis, autoimmune hepatitis, thyroiditis, insulitis, uveitis, orchitis, myasthenia gravis, idiopathic thrombocytopenic purpura, inflammatory bowel diseases (e.g., Crohn's disease and ulcerative colitis), systemic autoimmune diseases (e.g., rheumatoid arthritis (RA), sclerodema, and juvenile arthritis).

Autoimmunity is "suppressed" if one or more symptoms of an autoimmune disease is reduced or alleviated in a mammal (e.g., a human) affected by an autoimmune disease. Improvement, worsening, regression, or progression of a symptom may be determined by any objective or subjective measure known in the art. One of ordinary skill in the art will appreciate that the symptoms of autoimmune diseases vary based on the disease and location of the abnormal immune response. Symptoms that are common to several autoimmune diseases include, for example, fatigue, muscle and/or joint pain, muscle weakness, fever, swollen glands, inflammation, susceptibility to infections, weight loss or gain, allergies, digestive problems, blood pressure changes, and vertigo.

Thus, in one embodiment, the inventive method is used to treat an autoimmune disease in a mammal. As used herein, the terms "treatment," "treating," and the like, refer to obtaining a desired phaimacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the isolated IL-35 protein or IL-10-producing B-cells. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the IL-35 protein or IL-10-producing B-cells to elicit a desired response in the individual. For example, a therapeutically effective amount of an isolated IL-35 protein of the invention is an amount which induces IL-10 production and suppresses lymphocyte proliferation, which leads to the suppression of autoimmunity.

Alternatively, the pharmacologic and/or physiologic effect may be prophylactic, i.e., the effect completely or partially prevents an autoimmune disease or symptom thereof. In this respect, the inventive method comprises administering a "prophylactically effective amount" of the isolated IL-35 protein or IL-10-producing B-cells to a mammal that is predisposed to, or otherwise at risk of developing, an autoimmune disease. A "prophylactically effective amount" refers to an amount effective, at dosages and for periods of time necessary, to achieve a desired prophylactic result (e.g., prevention of disease onset or prevention of disease flare-ups).

When the inventive method comprises administering an IL-35 protein to a mammal, a composition comprising the IL-35 protein of the invention can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

When the inventive method comprises administering to a mammal an isolated IL-35 protein, the IL-35 protein is administered at a dose sufficient to induce the generation of B-cells that produce IL-10 and suppress autoimmunity in the mammal. A typical dose can be, for example, in the range of 0.001 to 1000 µg; however, doses below or above this exemplary range are within the scope of the invention. The daily parenteral dose can be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values), preferably from about 0.3 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 1 mg/kg of total body weight (e.g., about 3 µg/kg, about 15 µg/kg, about 75 µg/kg, about 300 µg/kg, about 900 µg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values). Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

When the inventive method comprises administering to a mammal B-cells which have been engineered to produce IL-10, a composition comprising the IL-10-producing B-cells can be administered to a mammal using standard cell transfer and immunotherapy techniques. Examples of such techniques include autologous cell therapy, allogeneic cell therapy, and hematopoietic stem cell therapy. In a preferred embodiment, a composition comprising IL-10-producing B-cells is administered to a mammal via adoptive transfer methods (see, e.g, Riley et al., *Immunity*, 30: 656-665 (2009), and Janeway et al., supra). The IL-10-producing B-cells can be administered in any suitable amount, so long as the introduction of the IL-10-producing B-cells suppresses autoimmunity in the mammal. A typical amount of cells administered to a mammal (e.g., a human) can be, for example, in the range of one million to 100 million cells however, amounts below or above this exemplary range are within the scope of the invention. For example, the daily dose of IL-10-producing B-cells can be about 1 million to about 50 million cells (e.g., about 5 million cells, about 15 million cells, about 25 million cells, about 35 million cells, about 45 million cells, or a range defined by any two of the foregoing values), preferably about 10 million to about 100 million cells (e.g., about 20 million cells, about 30 million cells, about 40 million, about 60 million cells, about 70 million cells, about 80 million cells, about 90 million cells, or a range defined by any two of the foregoing values), more preferably about 10 million cells to about 50 million cells (e.g., about 12 million cells, about 25 million cells, about 35 million cells, about 45 million cells, or a range defined by any two of the foregoing values).

The inventive method may be performed in combination with other existing therapies for autoimmune diseases. For example, the IL-35 protein or the IL-10-producing B-cells can be administered in combination with immunosuppressive or immunomodulating agents or other anti-inflammatory agents for the treatment or prevention of an autoimmune disease disclosed herein. In this respect, the inventive method can be used in combination with disease-modifying anti-rheumatic drugs (DMARD) (e.g., gold salts, sulphasalazine, antimalarias, methotrexate, D-penicillamine, azathioprine, mycophenolic acid, cyclosporine A, tacrolimus, sirolimus, minocycline, leflunomide, and glucocorticoids), a calcineurin inhibitor (e.g., cyclosporin A or FK 506), a modulator of lymphocyte recirculation (e.g., FTY720 and FTY720 analogs), an mTOR inhibitor (e.g., rapamycin, 40-O-(2-hydroxyethyl)-rapamycin, CCI779, ABT578, AP23573, or TAFA-93), an ascomycin having immunosuppressive properties (e.g., ABT-281, ASM981, etc.), corticosteroids, cyclophosphamide, azathioprene, methotrexate, leflunomide, mizoribine, mycophenolic acid, mycophenolate mofetil, 15-deoxyspergualine, or an immunosuppressive homologue, analogue or derivative thereof, immunosuppressive monoclonal antibodies (e.g., monoclonal antibodies to leukocyte receptors such as MHC, CD2, CD3, CD4, CD7, CD8, CD25, CD28, CD40. CD45, CD58, CD80, CD86, or their ligands), other immunomodulatory compounds, adhesion molecule inhibitors (e.g., LFA-1 antagonists, ICAM-1 or -3 antagonists, VCAM-4 antagonists, or VLA-4 antagonists), a chemotherapeutic agent (e.g., paclitaxel, gemcitabine, cisplatinum, doxorubicin, or 5-fluorouracil), anti-TNF agents (e.g. monoclonal antibodies to TNF such as infliximab, adalimumab, CDP870, or receptor constructs to TNF-RI or TNF-RII, such as ENBREL™ (Etanercept) or PEG-TNF-RI), blockers of proinflammatory cytokines, IL-1 blockers (e.g., KINERET™ (Anakinra) or IL-1 trap, AAL160, ACZ 885, and IL-6 blockers), chemokine blockers (e.g., inhibitors or activators of proteases), anti-IL-15 antibodies, anti-IL-6 antibodies, anti-CD20 antibodies, NSAIDs, and/or an anti-infectious agent.

The following examples further illustrate the invention but, of course, should not be construed as in any way limiting its scope.

EXAMPLE 1

This example demonstrates that a recombinant IL-35 protein suppresses proliferation of T and B lymphocytes in vitro and induces the production of IL-10 by B-cells.

A recombinant mouse IL-35 (rIL-35) construct was generated by PCR. The construct comprised a cDNA encoding the IL12p35-α subunit (p35) fused at the amino terminus to a nucleic acid sequence encoding an amino-terminal melittin (HBM) secretion signal sequence, and at the carboxy terminus to a cDNA encoding the β chain subunit of EBV-induced gene 3 (Ebi3). The rIL-35 construct also encoded a V5-epitope as well as Flag and polyhistidine tags to facilitate isolation and characterization of the recombinant protein. The construct was cloned into a 3.6 kilobase (kb) bicistronic pMIB vector containing a FLAG-IRES (internal ribosomal entry site) and V5-His sequences as described for the pMIB/V5-His A, B, and C Vector Kit (Life Technologies, Carlsbad, Calif.). Plasmids encoding flag-tagged p35 (p35) and V5-tagged Ebi3 (Ebi3) single chain recombinant proteins were engineered as controls. The rIL-35 construct was then transfected into High Five insect cells (Life Technologies, Carlsbad, Calif.), and stable transfectants were subjected to selection in Blasticidin S (80 µg/ml). Recombinant proteins secreted by the insect cells were purified on a Ni-NTA column, followed by differential centrifugation on centricon filtration units and sepharose chromatography. The recombinant proteins were further characterized by denaturing SDS gels, non-denaturing native gels, and HPLC.

CD4$^+$ T-cells were grown in cultures containing anti-CD3/CD28 antibodies, while B-cells were stimulated with lipopolysaccharide (LPS) (1.5 µg/ml). T-cells, B-cells, and cells from the mouse B-cell lymphoma line WEHI-279 were propagated in the presence or absence of rIL-35 (100 ng/ml). For some co-culture experiments, purified B-cells were stimulated with LPS (1.5 µg/ml) or a peptide fragment comprising amino acid residues 1-20 of human interphotoreceptor retinoid binding protein (IRBP$_{1-20}$) (40 µg/ml) and an anti-CD40 antibody (5 µg/ml) in the presence of rIL-35. The cells were then washed and co-cultured with LPS-stimulated B-cells or IRBP-stimulated lymphocytes. After 72 hours, cultures were pulsed with $^3$H-thymidine (0.5 µCi/10 µl/well) as described in Olkhanud et al., supra.

Figure 1C:
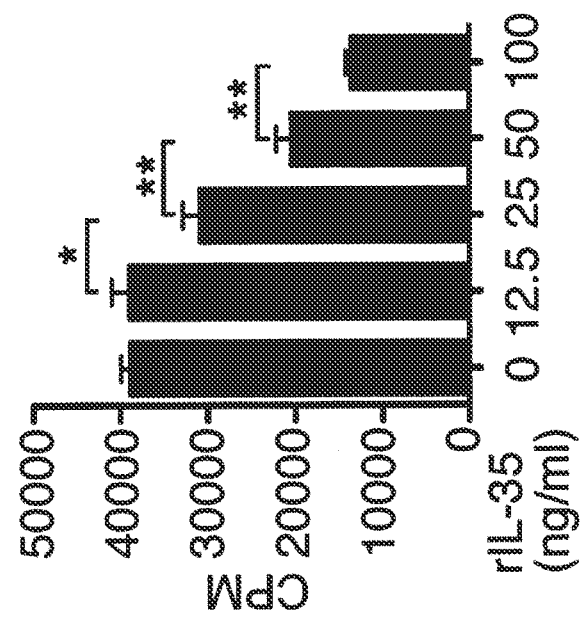
FIG. 1C is a graph which depicts experimental data illustrating the proliferation of WEHI-279 B-cells in response to varying concentrations of rIL-35.
Figure 1E:
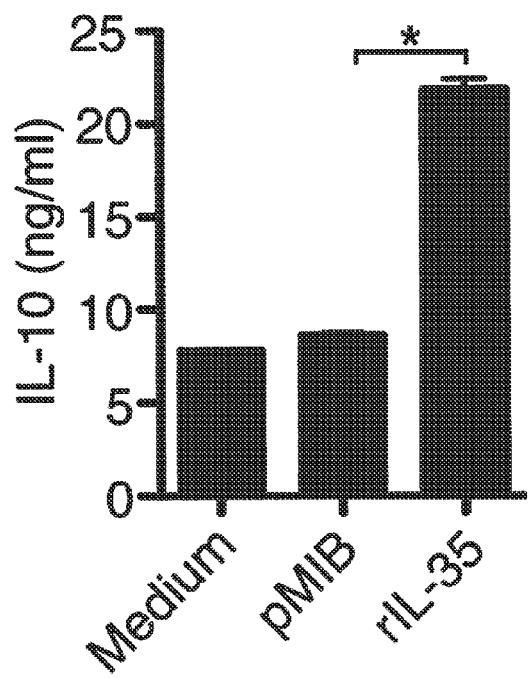
FIG. 1E is a graph which depicts experimental data illustrating the production of IL-10 by WEHI-279 B-cells in response to pMIB or rIL-35 as assayed by ELISA.

The rIL-35 protein suppressed the proliferation of T-cells and B-cells. To confirm the effect of IL-35 on B-cells, B220$^+$CD19$^+$ B-cells were purified from spleen and lymph nodes (LN) of C57BL/6 mice by fluorescence-activated cell sorting (FACS). Purified B-cells were stimulated with LPS and were propagated in the presence or absence of rIL-35 (100 ng/ml) as described above. rIL-35 significantly suppressed the proliferation of the LPS-stimulated primary B-cells as compared to cells transfected with an empty plasmid vector (pMIB) and plasmids expressing the IL12p35-α subunit or Ebi3 (see FIG. 1A). Mouse rIL-35 also inhibited proliferation of WEHI-279 cells in a dose-dependent manner (see FIGS. 1B and 1C), excluding the possibility that the suppressive effects derived from contaminating cells in the primary B-cell preparation.

rIL-35 significantly promoted IL-10 production by the B-cells (see FIG. 1D). WEHI-279 B-cells also produced IL-10 in response to rIL-35 (see FIG. 1E), indicating that the conversion of the immature B-cells into regulatory B-cells (Bregs) was directly mediated by rIL-35. Furthermore, rIL-35 caused Bregs to up-regulate expression of the p35 protein, which was primarily evident in IL-10-producing Bregs, as well as p35 and Ebi3 mRNA. These results suggest that rIL-35 bestowed onto Bregs the capacity to produce IL-35 ("i35-Bregs"). The fact that IL-35 can convert B-cells into Bregs or i35-Bregs and naïve primary CD4 T-cells into Tregs, suggests that IL-35 mediates similar biological effects in B- and T-cells.

Figure 1F:
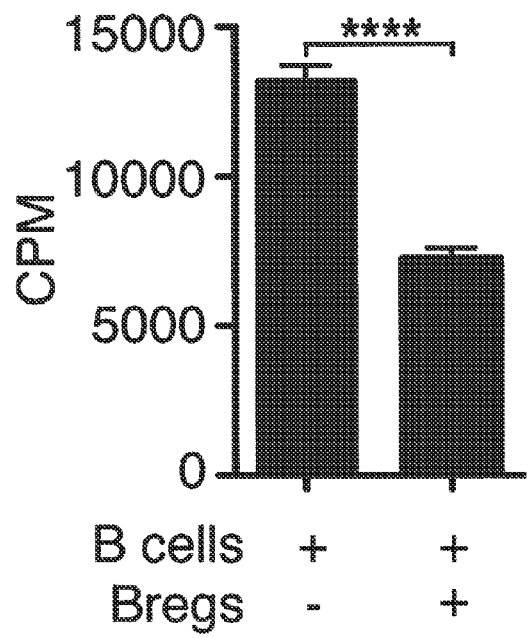
FIG. 1F is a graph which depicts experimental data illustrating that sorted primary B-cells stimulated with rIL-35 (Bregs) suppressed the proliferation of LPS-stimulated B-cells.

To directly establish that the IL-35-induced Bregs suppress B-cell proliferation, sorted primary B-cells were stimulated with rIL-35 and suppressed the proliferation of LPS-stimulated B-cells (see FIG. 1F) and TCR-activated T effector cells in co-culture experiments.

The results of this example demonstrate that IL-35 suppresses lymphocyte proliferation, particularly T- and B-cell proliferation, and can convert primary B-cells into IL-10-expressing regulatory B-cells.

EXAMPLE 2

This example demonstrates that IL-35 mediates its biological effects on B-cells through a novel IL-35 receptor.

IL-35 signal transduction and IL-35 cognate receptors expressed on lymphocytes were examined. Specifically, WEHI-279 cells were transfected with siRNA that specifically targets receptor subunits utilized by IL-12 family cytokines, including IL-12Rβ1, IL-12Rβ2, IL-27Rα, and gp130.

Figure 2A:
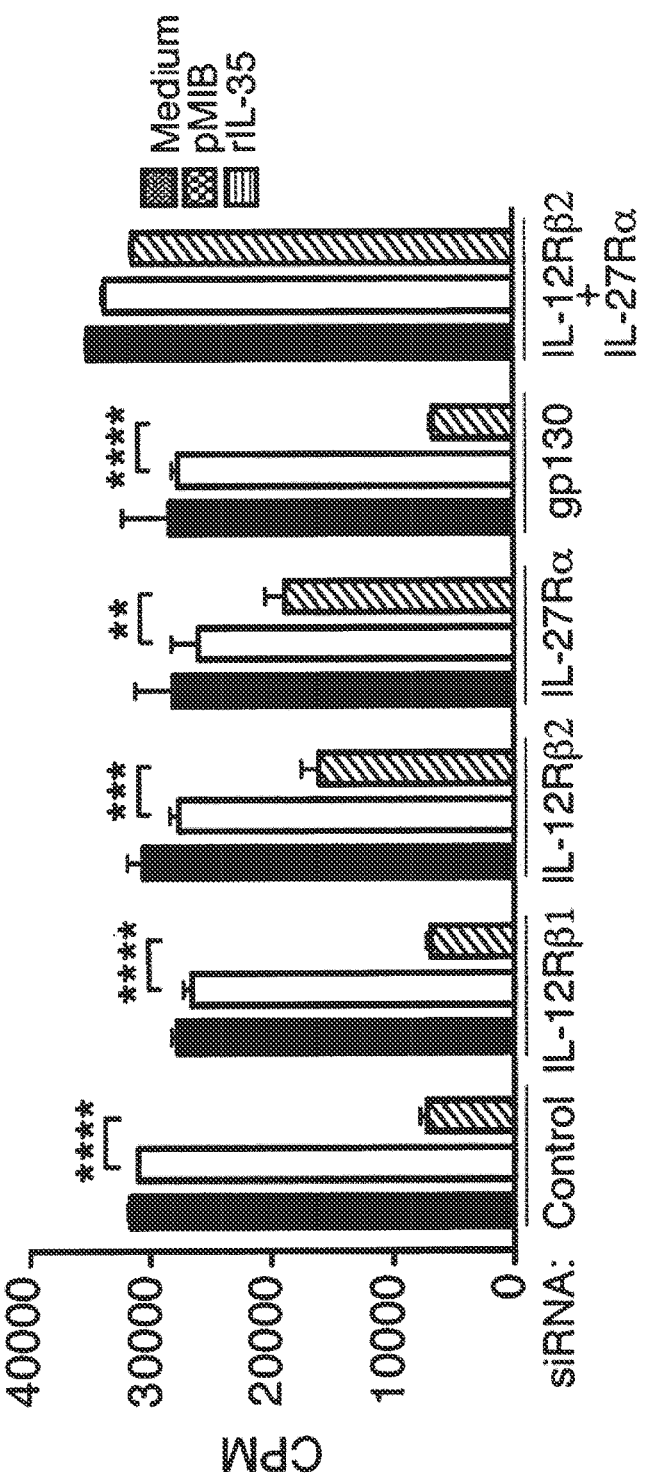
FIG. 2A is a graph which depicts experimental data illustrating the requirement of each IL-12 family receptor subunit for rIL-35-mediated inhibition of B-cell proliferation, as measured by a $^3$H-thymidine incorporation assay.
Figure 2B:
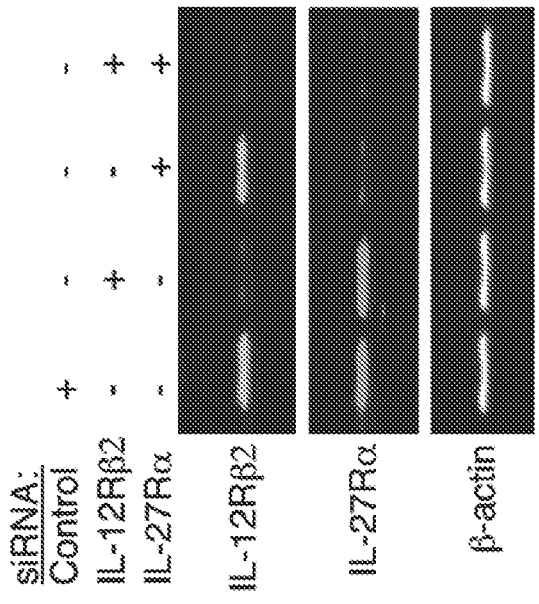
FIG. 2B is a graph which depicts experimental data illustrating the requirement of each IL-12 family receptor subunit for B-cell IL-10 production, as measured by an ELISA assay.
Figure 2C:
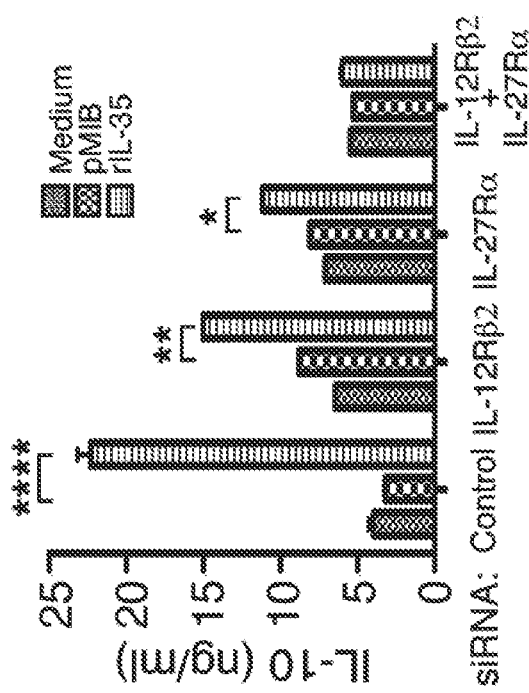
FIG. 2C is an image which depicts experimental data illustrating the co-expression of IL27Rα and IL-12Rβ2 on WEHI-279 B-cells, as detected by RT-PCR.

The requirement of each receptor subunit for rIL-35-mediated inhibition of proliferation or IL-10 production was assessed by an [$^3$H]-thymidine-incorporation assay or ELISA, respectively. Silencing of IL-12Rβ1 or the gp130 subunit did not affect rIL-35-mediated inhibition of B-cell proliferation (see FIG. 2A) or its enhancement of IL-10 production (see FIG. 2B). In contrast, silencing IL-12Rβ2 and IL-27Rα completely abrogated the effects of rIL-35 on B-cell proliferation and IL-10 production (see FIGS. 2A and 2B). Both IL-12Rβ2 and IL-27Rα were expressed on stimulated B-cells, as determined by RT-PCR (see FIG. 2C). Reciprocal coimmunoprecipitation analysis confirmed the interaction between IL-12Rβ2 and IL-27Rα in activated B-cells. These results suggest that the IL-12Rβ2/IL-27Rα hetero-dimer is the functional IL-35 receptor which mediates the biological effects of IL-35 in the mouse.

To determine the STAT proteins utilized in response to IL-35 signaling, activated B- or T-cells were cultured in the presence of pMIB, rIL-35, or IL-12 as described above, and STAT activation was analyzed by FACS or Western blotting. Both Western and FACS analysis revealed that rIL-35 preferentially activates STAT1, STAT3 and STAT4 in T-cells (see FIG. 2E), while in B-cells rIL-35 signals primarily through STAT1 and STAT3 but not STAT4 (see FIG. 2D), thereby indicating differential utilization of these STATs in T- and B-cells by IL-35.

The results of this example demonstrate that the IL-12Rβ2/IL-27Rα hetero-dimer is the functional IL-35 receptor. The results of this example also demonstrate that the IL-35 signal is transmitted through activation of STAT1, STAT3, and STAT4 pathways in T-cells and through activation of STAT1 and STAT3 in B-cells.

EXAMPLE 3

This example demonstrates a method of suppressing experimental autoimmune uveitis (EAU) in a mouse treated with IL-35.

Noninfectious uveitis is a potentially blinding intraocular inflammatory disease mediated by autoreactive Th17 and Th1 cells (see, e.g., Nussenblatt et al., *Int. Ophthalmol.*, 14: 303-308 (1990); Amadi-Obi, *Nat. Med.*, 13: 711-718 (2007); and Luber et al., *J. Exp. Med.*, 205: 799-810 (2008)). A rodent model of the disease, experimental autoimmune uveitis (EAU), shares essential features of human uvveitis (see, e.g., Caspi et al., *J. Immunol.*, 140: 1490-1495 (1988), and Nussenblatt et al., *Invest. Ophthalmol. Vis. Sci.*, 32: 3131-3141 (1991)).

EAU was induced in C57BL/6 mice by active immunization with 150 µg bovine interphotoreceptor retinoid-binding protein (IRBP) and 300 µg of a peptide fragment containing amino acid residues 1-20 of human IRBP ($IRBP_{1-20}$) in 0.2 ml emulsion 1:1 v/v with Complete Freund's adjuvant (CFA) containing *Mycobacterium tuberculosis* strain H37RA (2.5 mg/ml). Mice also received *Bordetella pertussis* toxin (0.3 µg/mouse) concurrent with immunization. Clinical disease was established and scored by fundoscopy as described previously (see e.g., Fillatreau et al., *Nat. Rev. Immunol.*, 8: 391-397 (2008); Carter et al, supra; and Ding et al., supra).

Mice received 100 µg/mouse pMIB or rIL-35 concurrent with IRBP immunization six days after EAU induction. Disease progression was monitored by fundoscopy (see, e.g., Paques et al., *Invest. Ophthalmol. Vis. Sci.*, 48: 2769-2774 (2007), Lu et al., *Invest. Ophthalmol. Vis. Sci.*, 52: 4671-4677 (2011), and Myung et al., *Am. J. Ophthalmol.* (2011), epublication in advance of print). To assess disease severity and EAU scores, a well-established semi-quantitative grading scheme was used that is based on the degrees of inflammatory infiltration and degeneration at the retina, choroid, and optic nerve disc (see, e.g., Chan et al., *J. Autoimmun.*, 3: 247-255 (1990), and Xu et al., *Exp. Eye Res.*, 87: 319-326 (2008)). At 21 days post-immunization, intracellular cytokine expression by $CD4^+$ T-cells and B-cells in the blood of IRBP-immunized mice was assessed by FACS. In addition, sorted $CD19^+$ B-cells from day-21 IRBP-immunized mice were re-activated with $IRBP_{1-20}$ and an anti-CD40 antibody for three days and rIL-35-induced expression of IL-10 was analyzed by FACS, quantitative PCR, and RT-PCR. $CD19^+$ B-cells were then co-cultured with draining lymph node cells of EAU mice (1:5) for four days in the presence of IRBP, and the effects of rIL-35 on T-cell proliferation, expression of Foxp3, or p35 and Ebi3, were assessed by [$^3H$]-thymidine incorporation assay, intracellular cytokine staining assay, or RT-PCR.

Figure 3B:
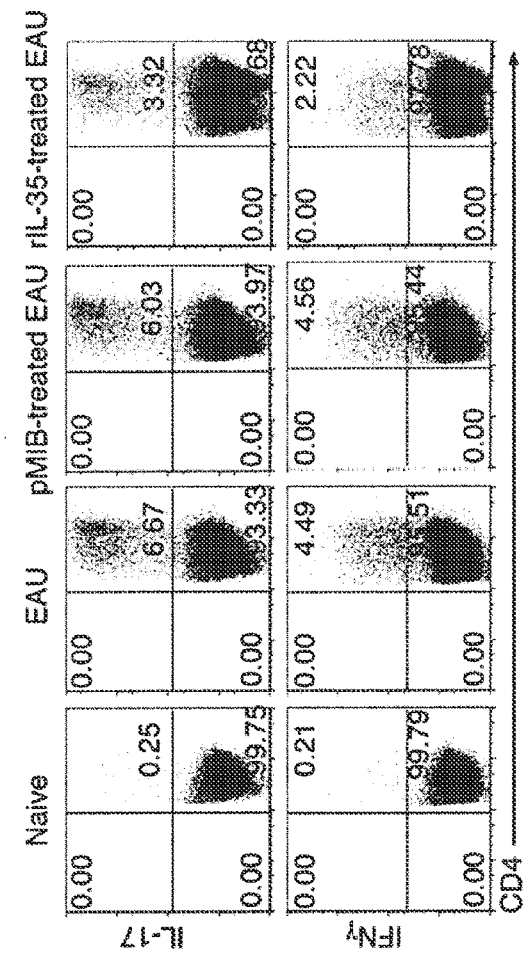
FIG. 3B is a diagram which depicts experimental data illustrating FACS analysis of intracellular cytokine expression by $CD4^+$ T-cells in the blood of IRBP-immunized mice at 21 days post-immunization.
Figure 3A:
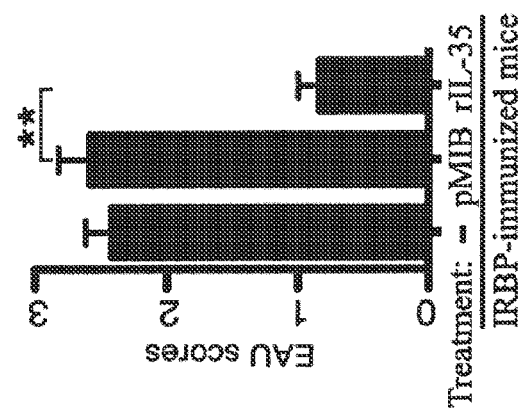
FIG. 3A is a graph which depicts experimental data illustrating the EAU disease scores of IRBP-immunized mice treated with rIL-35 or controls.
Figure 3C:
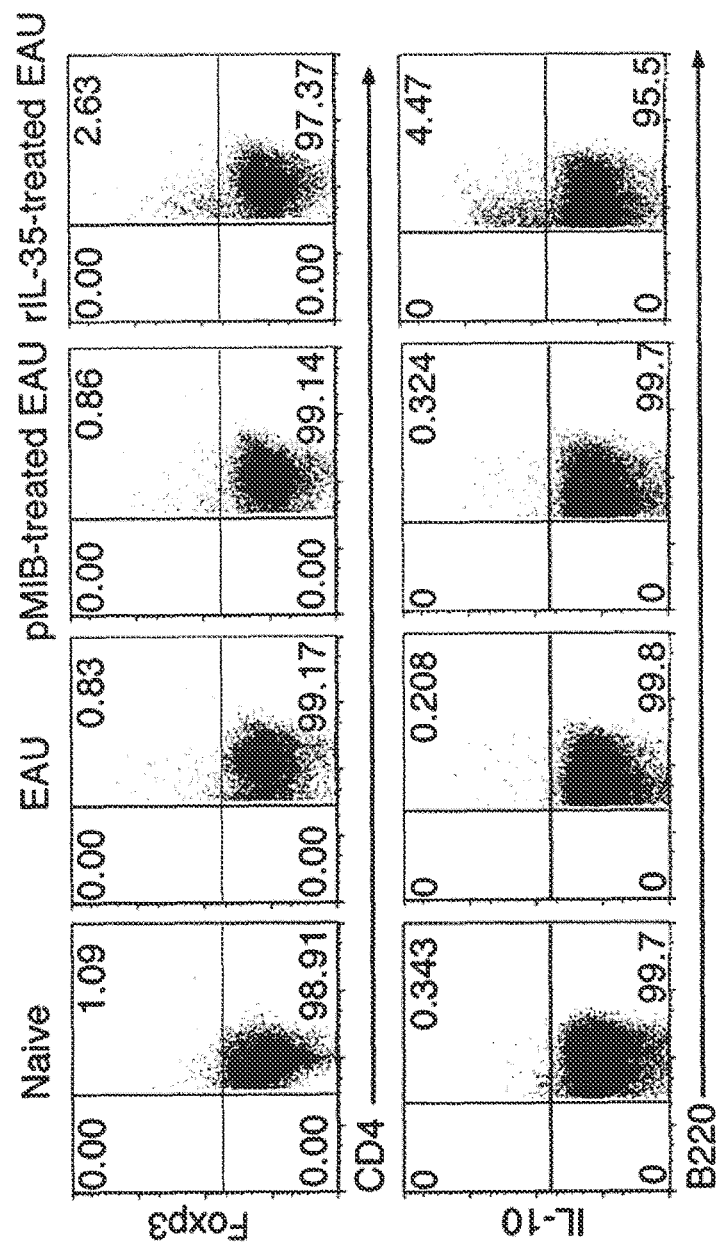
FIG. 3C is a diagram which depicts experimental data illustrating FACS analysis of intracellular cytokine expression by $CD4^+$ B-cells in the blood of IRBP-immunized mice at 21 days post-immunization.

By 21 days post-immunization, Fundus images of control mice or mice that received pMIB revealed severe inflammation with papilledema, retinal vasculitis, and retinal and choroidal infiltrates. In contrast, rIL-35-treated mice exhibited very mild EAU with significantly lower EAU scores (see FIG. 3A). Amelioration of EAU in rIL-35-treated mice was accompanied by substantial diminution of percentages of Th17 and Th1 cells (see FIG. 3B), with concomitant increases of Tregs and Bregs in the blood (see FIG. 3C).

Figure 3E:
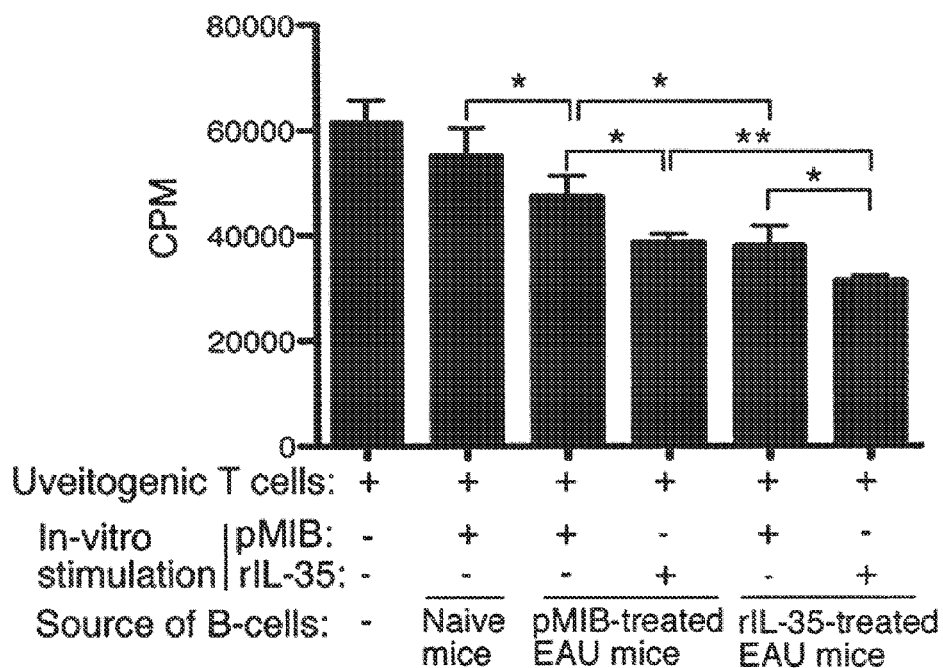
FIG. 3E is a graph which depicts experimental data illustrating the effects of Bregs re-activated with IRBP in the presence of rIL-35 on T-cell proliferation as measured by a [$^3$H]-thymidine incorporation assay.

In addition, mice treated with rIL-35 during EAU induction contained increased numbers of Bregs in-vivo, and ex-vivo stimulation with IL-35 further increased the numbers of Bregs and production of IL-10 (see FIG. 3D). Bregs induced by rIL-35 during EAU suppressed the proliferation of IRBP-specific uveitogenic effector T-cells (Teff) in co-culture experiments, and the inhibitory effect was enhanced if the Bregs were re-activated with IRBP in the presence of rIL-35 (see FIG. 3E). The Bregs also promoted conversion of the Teff cells into inducible Tregs (iTregs) in an IL-35-dependent manner, thereby suggesting an additional mechanism that contributes to the suppression of EAU by rIL-35 and Bregs. In addition, rIL-35 appeared to induce expansion of the novel i35-Breg subpopulation during EAU, thereby suggesting a positive feedback loop that may function to amplify the numbers of Bregs in vivo.

Figure 3F:
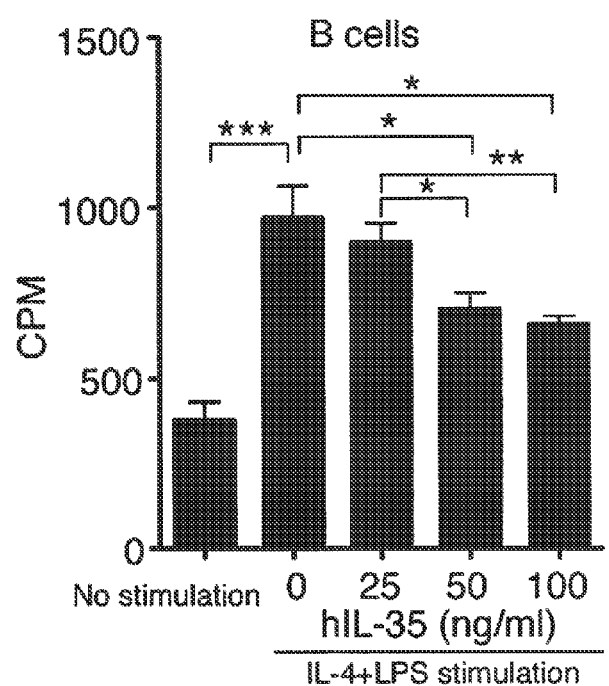
FIG. 3F is a graph which depicts experimental data illustrating the effects of human IL-35 on the proliferation of human CD19$^+$ B-cells stimulated with PMA or LPS and IL-4.

Activated $CD19^+$ B-cells from un-immunized or EAU mice were co-cultured with T-cells from mice with EAU for four days in the presence of IRBP, then adoptively transferred into naïve syngeneic mice and assessed for EAU development by Fundoscopy. T-cells co-cultured with B-cells from normal or EAU (no treatment) mice induced severe EAU, while T-cells co-cultured with B-cells from rIL-35-treated mice could not transfer EAU. Human IL-35 induced conversion of human B-cells into Bregs and inhibited the proliferation of human B-cells (see FIG. 3F).

The results of this example demonstrate that autoimmunity can be suppressed in a mammal by administering an IL-35 protein, which induces the production of IL-10-producing regulatory B-cells in the mammal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended teams (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

55

The invention claimed is:

1. A method of preparing B-cells that produce interleukin-10 (IL-10), which method comprises contacting one or more B-cells ex vivo with an isolated interleukin-35 (IL-35) protein, and culturing the one or more B-cells under conditions to provide one or more B-cells that produce IL-10.

2. The method of claim 1, wherein the B-cells that produce IL-10 are regulatory B-cells.

3. The method of claim 1, wherein the isolated IL-35 protein is a recombinant fusion protein comprising an IL-12p35 α subunit protein and an Epstein-Barr virus (EBV)-induced gene 3 (Ebi3) protein.

4. The method of claim 1, wherein the one or more B-cells are primary B-cells.

5. A method of suppressing the proliferation of lymphocytes in vitro or in vivo, which method comprises contacting the lymphocytes with one or more B-cells prepared according to claim 1, whereby the proliferation of lymphocytes is suppressed.

6. The method of claim 5, wherein the isolated IL-35 protein is a recombinant fusion protein comprising an IL-12p35 α subunit protein and an Epstein-Barr virus (EBV)-induced gene 3 (Ebi3) protein.

7. The method of claim 5, wherein the suppressed lymphocytes are T-cells.

8. The method of claim 5, wherein the suppressed lymphocytes are B-cells.

9. The method of claim 5, wherein the lymphocytes are located in a mammal.

10. The method of claim 9, wherein the mammal is a mouse or a human.

11. The method of claim 5, wherein the isolated IL-35 protein is recombinant.

12. The method of claim 5, wherein the isolated IL-35 protein is a recombinant protein comprising an IL-12p35 α subunit protein and an Epstein-Barr virus (EBV)-induced gene 3 (Ebi3) protein.

13. A method of suppressing autoimmunity in a mammal, which method comprises administering to a mammal B-cells which produce IL-10 and are prepared according to claim 1, whereby autoimmunity is suppressed in the mammal.

14. The method of claim 13, wherein the B-cells that produce IL-10 are regulatory B-cells.

15. The method of claim 13, wherein the mammal has an autoimmune disease.

16. The method of claim 15, wherein the autoimmune disease is uveitis, systemic lupus erythematosis, scleroderma, Crohn's disease, psoriasis, or rheumatoid arthritis.

17. The method of claim 1, wherein the isolated IL-35 protein is recombinant.

18. The method of claim 1, wherein the isolated IL-35 protein is a recombinant protein comprising an IL-12p35 α subunit protein and an Epstein-Barr virus (EBV)-induced gene 3 (Ebi3) protein.

19. A method of producing IL-10, which method comprises contacting one or more B-cells ex vivo with an isolated interleukin-35 (IL-35) protein, and culturing the one or more B-cells under conditions to provide one or more B-cells that produce IL-10.

20. The method of claim 19, wherein the B-cells that produce IL-10 are regulatory B-cells.

21. The method of claim 19, wherein the isolated IL-35 protein is a recombinant fusion protein comprising an IL-12p35 α subunit protein and an Epstein-Barr virus (EBV)-induced gene 3 (Ebi3) protein.

22. The method of claim 19, wherein the one or more B-cells are primary B-cells.

23. The method of claim 19, wherein the isolated IL-35 protein is recombinant.

24. The method of claim 19, wherein the isolated IL-35 protein is a recombinant protein comprising an IL-12p35 α subunit protein and an Epstein-Barr virus (EBV)-induced gene 3 (Ebi3) protein.

* * * * *